(12) United States Patent
Geddes et al.

(10) Patent No.: US 7,569,018 B1
(45) Date of Patent: Aug. 4, 2009

(54) APPARATUS AND METHOD FOR NONINVASIVELY DETECTING THE QUALITY OF CARDIAC PUMPING

(75) Inventors: Leslie A. Geddes, Lafayette, IN (US);
Kirk S. Foster, Lafayette, IN (US);
Rebecca A. Roeder, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 39 days.

(21) Appl. No.: 10/368,180

(22) Filed: Feb. 18, 2003

(51) Int. Cl.
*A61B 5/00* (2006.01)
(52) U.S. Cl. ..................................... 600/485; 600/500
(58) Field of Classification Search ......... 600/500–503, 600/485, 322–324, 478–480
See application file for complete search history.

(56) References Cited

U.S. PATENT DOCUMENTS

| | | | |
|---|---|---|---|
| 3,848,574 A | 11/1974 | Fujikawa et al. | |
| 3,978,849 A * | 9/1976 | Geneen | 600/503 |
| 4,074,710 A * | 2/1978 | Tiep | 600/502 |
| 4,367,752 A | 1/1983 | Jimenez et al. | |
| 4,653,498 A * | 3/1987 | New et al. | 600/324 |
| 4,685,464 A * | 8/1987 | Goldberger et al. | 600/344 |
| 4,819,752 A * | 4/1989 | Zelin | 600/322 |
| 4,860,759 A | 8/1989 | Kahn et al. | |
| 4,867,170 A * | 9/1989 | Takahashi | 600/490 |
| 4,867,442 A | 9/1989 | Matthews | |
| 5,111,817 A | 5/1992 | Clark et al. | |
| 5,237,997 A * | 8/1993 | Greubel et al. | 600/485 |
| 5,368,026 A * | 11/1994 | Swedlow et al. | 600/323 |
| 5,431,170 A * | 7/1995 | Mathews | 600/479 |
| 5,579,763 A | 12/1996 | Weil et al. | |
| 5,582,580 A * | 12/1996 | Buckman et al. | 601/41 |
| 5,735,799 A * | 4/1998 | Baba et al. | 600/500 |

(Continued)

FOREIGN PATENT DOCUMENTS

EP   87101135.9   8/1988

(Continued)

OTHER PUBLICATIONS

Zijlstra, Willem Gerrit, *Fundamentals and Applications of Clinical Oximetry*, Van Gorcum & Comp. N.V., c. 1951 (cover and 2 pages).

(Continued)

*Primary Examiner*—Robert L Nasser
(74) *Attorney, Agent, or Firm*—William F. Bahret

(57) ABSTRACT

An auditory pulse monitor for noninvasively detecting the amplitude of arterial pulses on a beat-by-beat basis. A lightweight optical sensor including a light source and photodetector is adapted for application to the skin surface of a subject over a tissue bed containing an arterial supply. The photodetector generates an output signal proportional to the amplitude of an arterial pulse, and an electronic circuit connected to the photodetector generates a signal having a frequency proportional to the photodetector output signal level. A speaker or other audio indicator connected to the electronic circuit generates an audible tone indicating the amplitude of the arterial pulse. Another aspect of the invention is an improvement in automated or automatic external defibrillators (AEDs). An AED is disclosed which optically detects arterial pulses after delivering a defibrillation shock and signals the need for CPR if it detects inadequate cardiac pumping following successful defibrillation.

56 Claims, 5 Drawing Sheets

U.S. PATENT DOCUMENTS

| | | |
|---|---|---|
| 5,776,071 A | 7/1998 | Inukai et al. |
| 5,782,879 A | 7/1998 | Rosborough et al. |
| 5,830,137 A | 11/1998 | Scharf |
| 6,055,447 A | 4/2000 | Weil et al. |
| 6,071,237 A | 6/2000 | Weil et al. |
| 6,080,110 A | 6/2000 | Thorgersen |
| 6,125,299 A | 9/2000 | Groenke et al. |
| 6,258,046 B1 | 7/2001 | Kimball et al. |
| 6,340,349 B1 * | 1/2002 | Archibald et al. ........... 600/494 |
| 6,356,785 B1 | 3/2002 | Snyder et al. |
| 6,398,744 B2 | 6/2002 | Bystrom et al. |
| 6,440,082 B1 | 8/2002 | Joo et al. |
| 6,477,406 B1 | 11/2002 | Turcott |
| 6,572,636 B1 * | 6/2003 | Hagen et al. ................ 600/500 |
| 2001/0047140 A1 | 11/2001 | Freeman |
| 2001/0056227 A1 | 12/2001 | Gopinathan et al. |
| 2002/0165585 A1 | 11/2002 | Dupelle et al. |
| 2002/0188210 A1 * | 12/2002 | Aizawa ...................... 600/503 |
| 2003/0060723 A1 | 3/2003 | Joo et al. |
| 2004/0116969 A1 | 6/2004 | Owen et al. |
| 2004/0158158 A1 * | 8/2004 | Jensen et al. ................ 600/476 |
| 2006/0264726 A1 | 11/2006 | Mannheimer |

FOREIGN PATENT DOCUMENTS

| | | |
|---|---|---|
| EP | 0305080 A | 3/1989 |
| EP | 0947163 A2 | 10/1999 |
| EP | 1199085 A2 | 4/2002 |
| WO | WO2004/073787 | 9/2004 |

OTHER PUBLICATIONS

*Zoll AED Plus Administrator's Guide*, Zoll Medical Corporation, © 2002.

Geddes, L.A., M.E., Ph.D., *The Direct and Indirect Measurements of Blood Pressure*, 1970, Year Book Medical Publishers, Inc., Chicago, Illinois, pp. 70-99.

Nuhr et al., "Forehead $SpO_2$ Monitoring Compared to Finger $SpO_2$ Recording in Emergency Transport," *Anaesthesia*, 2004, vol. 59, pp. 390-393.

Tyco Healthcare advertisement for Max-Fast Forehead Sensor.

Tyco Heathcare advertisement for N-595 Pulse Oximeter.

BioSpace article on Nellcor MAX-FAST Forehead Sensor.

Texas Advanced Optoelectronic Solutions Production Data on TSL235 Light-to-Frequency Converter.

Supplementary European Search Report, dated Apr. 15, 2009, in Application No. EP04712333 (5 pages).

* cited by examiner

APPARATUS AND METHOD FOR NONINVASIVELY DETECTING THE QUALITY OF CARDIAC PUMPING

BACKGROUND OF THE INVENTION

This invention relates to devices and methods for monitoring cardiac pumping, and more particularly to a new device and method for noninvasively detecting the quality of cardiac pumping resulting from cardiopulmonary resuscitation (CPR) or from automatic external defibrillation.

CPR is a well known and valuable emergency procedure for reviving a person suffering cardiac arrest. When the heart stops pumping blood, the resulting lack of fresh oxygen to the brain can cause brain damage within minutes and death can soon follow. CPR involves repetitive chest compression coordinated with mouth-to-mouth breathing, and its effectiveness depends on coordinated delivery of adequate chest compressions and rescue breaths and, to a large extent, on the quality and timing of the chest compressions. Much attention has been devoted to the subject and particularly to techniques for training emergency medical personnel as well as ordinary citizens how to perform CPR properly even under stress associated with treating a life-threatening condition and even if fatigued from a sustained effort.

A pressure-sensitive chest pad has been proposed as a feedback tool for a rescuer administering chest compressions during CPR. For example, an automatic external defibrillator (AED) recently introduced by Zoll Medical Corporation, the Zoll AED PLUS, is available with a chest pad with which it is said to monitor rate and depth of chest compressions when the rescuer presses on the pad. Voice and visual prompts encourage a compression depth of 1½-2 inches. However, the AED gives no indication of the effectiveness of pumping of blood. One of the rescuers is prompted to check the victim for the presence of a pulse or other signs of circulation such as normal breathing, movement, coughing or color of the lips or skin. Such methods do not give the typical human rescuer feedback fast enough to enable the rescuer to vary the style of chest compression in order to optimize blood pumping.

Perfusion monitors designed to measure blood gases, such as the monitor proposed in U.S. Pat. No. 5,579,763 to Weil et al., can take minutes to respond and thus also fail to provide sufficiently rapid feedback, e.g., beat-by-beat feedback, for a typical human rescuer.

A need exists for a simple and practical device which can give a positive indication of the effectiveness of blood pumping in response to chest compression during CPR. There is also a need for a simple and practical way to noninvasively detect cardiac pumping following defibrillation with an AED.

Electromechanical dissociaton (EMD) is a condition in which the R waves of the ECG either do not produce ventricular contractions or produce extremely weak contractions, resulting in little or no blood pumping. The condition is sometimes known as pulseless electrical activity (PEA). It occurs frequently because ventricular fibrillation is often not treated with CPR for a period of time or the CPR is inadequately performed. In such situations, the heart muscle, being deprived of oxygenated blood because there is no blood pumping, becomes injured and consequently beats weakly or not at all after successful defibrillation. Thus, even though an AED may indicate that the criterion for successful defibrillation has been met, namely abolishing the high-frequency fibrillation waves in the ECG, the heart muscle cannot respond adequately to the resulting R waves and the victim is likely to die as a result if other intervention is not promptly provided.

Another postdefibrillation situation for failure of the ventricles to contract is atrioventricular (A-V) block. A-V block is not uncommon immediately after successful ventricular defibrillation and no ventricular pulses are produced.

The appropriate therapy for EMD and A-V block is the prompt application of effective CPR.

SUMMARY OF THE INVENTION

According to one aspect of the present invention, a beat-by-beat auditory pulse monitor allows a rescuer who is administering CPR to evaluate the effectiveness of each chest compression to pump blood. The inventive device detects the arterial pulse resulting from each chest compression and generates an audible tone indicating the amplitude of each pulse. An optical sensor including a light source and photodetector is applied to a skin surface of a subject over a tissue bed containing an artery, preferably where there is a substantially planar underlying bone surface, such as the forehead, which reflects incident radiation. In a preferred embodiment, the frequency of the audible tone is proportional to the instantaneous amplitude of the pulse generated by that chest compression, varying continuously over a cardiac cycle. Thus, the rescuer has an immediate feedback signal that informs him/her of the effectiveness of each chest compression and he/she can modify the compression style to obtain the largest amplitude pulse, identified by the tone with the highest pitch.

Another aspect of this invention is an improvement in automated or automatic external defibrillators (AEDs). An improved AED according to the present invention detects arterial pulses after delivering a defibrillation shock and signals the need for CPR if it detects inadequate cardiac pumping following successful defibrillation.

Other objects and advantages of the present invention will become more apparent from the following detailed description of preferred embodiments in conjunction with the accompanying drawings.

DETAILED DESCRIPTION OF PREFERRED EMBODIMENTS

Figure 1:
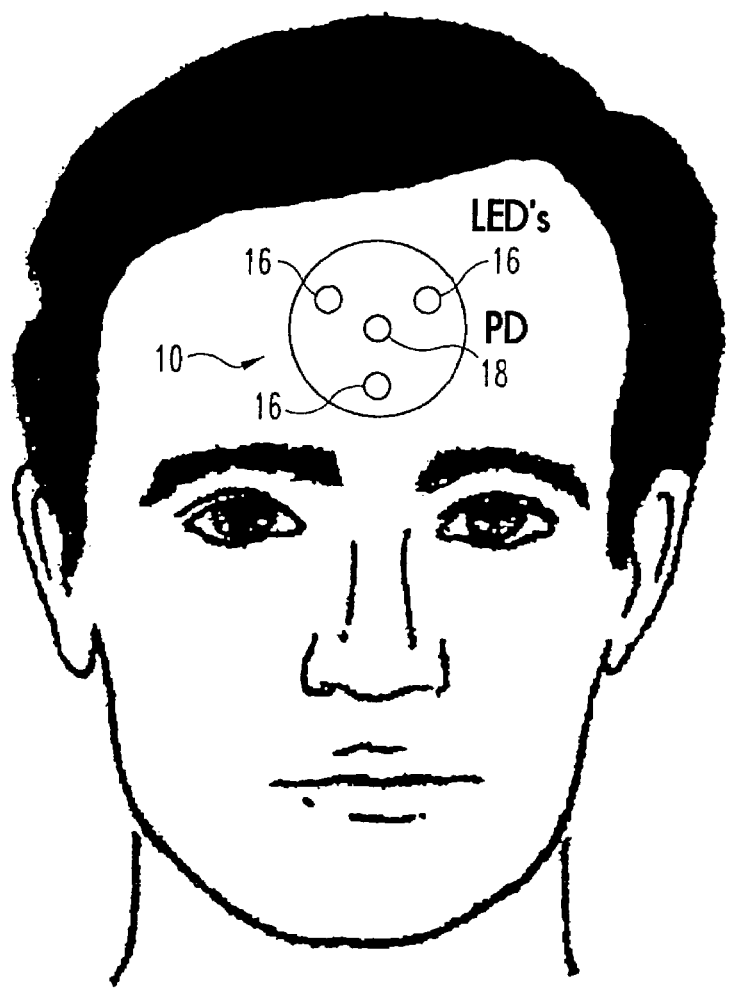
FIG. 1 is a diagram of one embodiment of the optical sensor portion of a pulse monitor according to the present invention, shown from the rear in position on the forehead of a human subject.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and such further applications of the principles of the invention as illustrated therein being contemplated as would normally occur to one skilled in the art to which the invention relates.

Figure 2:
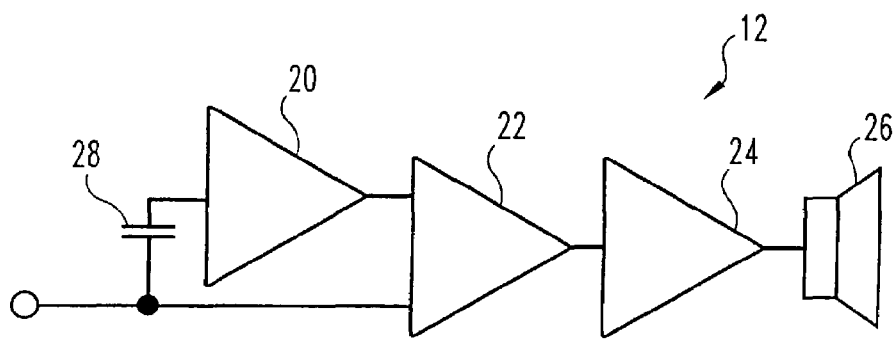
FIG. 2 is a block diagram of one embodiment of a circuit to which the optical sensor of FIG. 1 is connected in an auditory pulse monitor according to the present invention.

Referring to FIGS. 1 and 2, one embodiment of an auditory pulse monitor according to the present invention includes an optical sensor 10 connected to a circuit 12. The small optical sensor is preferably adapted for quick placement on the forehead of a subject 14 and includes one or more light-emitting diodes (LEDs) 16 that surround a photodetector 18 as shown in FIG. 1. The LEDs are preferably infrared devices, e.g., PDI-E801 or PDI-E804 880 nm LEDs available from Photonic Detectors, Inc. The LEDs and photodetector are preferably matched to operate at a desired wavelength. One example of a suitable photodetector is a Fairchild Semiconductor QSD723 phototransistor, with a peak sensitivity at 880 nm. Another suitable operating wavelength is 805 nm. At 805 nm oxygenated blood ($HbO_2$) and blood without oxygen (Hb) transmit equally well. Therefore the pickup has no oxygen-saturation error. An advantage of either of the example wavelengths is that there are virtually no environmental light sources in this infrared region.

Although the specific placement of the optical sensor on the forehead of a human subject is not critical, the maximum amplitude for pulse detection has been found to occur on or near the center of the forehead, slightly above the eyebrows. With the LEDs equally spaced about a photodetector as in FIG. 1, the sensor has rotational symmetry and is therefore substantially insensitive to orientation on the skin surface. It is presently preferred to have such an arrangement with three LEDs. It is particularly desirable to have a light-weight sensor in order to minimize movement artifacts; the preferred optical sensor preferably weighs only about 2 grams. The optical sensor may be held on the subject's forehead with an elastic band, or by suction applied to an annular chamber around the LEDs and photodetector, or with double-sided tape such as Stomaseal from 3M.

Figure 3:
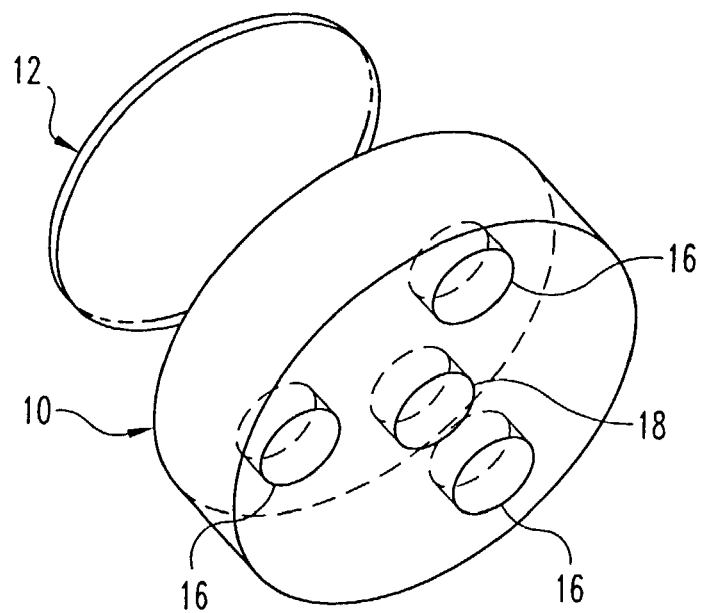
FIG. 3 is an exploded, front perspective view of one embodiment of a self-contained pulse monitor according to the present invention.

Circuit 12 includes a first amplifier 20 connected to a voltage-controlled oscillator (VCO) 22 the output of which is connected to a second amplifier 24 and a loudspeaker 26 as shown in FIG. 2. The circuit also contains appropriate circuitry for driving the LEDs simultaneously, and may be contained in a small case together with a battery power source connected by a cable to the optical sensor such that the auditory pulse monitor is a self-contained device for rapid application in the field. Alternatively, as shown in FIG. 3, a self-contained unit may be constructed with circuit 12, including a battery power source, on a printed circuit board affixed to the rear surface of sensor 10. The LEDs and photodetector may be retained within a molded plastic disc as shown in FIG. 3, with cylindrical through-holes formed in the plastic disc to receive and align the LEDs and photodetector, which may also be directly electrically connected to conductive traces on the circuit board.

Arterial pulses are detected by reflectance from the tissues in the tissue bed under the optical pickup. The photodetector may be AC-coupled via capacitor 28 and amplifier 20 to the VCO, which produces a frequency proportional to the voltage applied to it, and may also be DC-coupled as shown. The circuit is designed such that, with no arterial pulse, it produces a low-frequency tone when the pickup is on the forehead to indicate that the pickup is in place. The circuit also provides a characteristic tone that indicates that the sensor is not on the body, i.e., a sensor-off tone.

The LEDs may be pulsed on and off to reduce power consumption. For example, in one embodiment having two PDI-E801 LEDs connected in series, the LEDs are pulsed on at a pulse repetition rate of 100 Hz with a pulse width of 200 µS, resulting in a 2% duty cycle, and at a current level of approximately 400 mA. A high speed op-amp, e.g., Analog Devices AD823, may be connected as a buffer between the phototransistor, e.g., Fairchild QSD723, and a sample-and-hold, e.g., Maxim MAX394. The phototransistor output signal is preferably sampled near the end of the LED ON time, e.g., beginning at 190 µS after the start of the LED ON pulse, with a sampling interval of 2.5 µS as one example. The sampling delay compensates for the relatively slow response time of the phototransistor, and, by sampling only near the end of the LED ON time, output ripple is minimized. The sampled signal is filtered with first order reconstruction filters, e.g., Analog Devices AD823, with a bandwidth from 0.5 Hz to 30 Hz, and the resulting analog signal, representing the pulsatile changes in blood volume adjacent to the sensor's optics, may be supplied to a VCO and audible device as described above.

In operation, each time the subject's chest is compressed and blood is pumped, the frequency of the tone increases in proportion to the instantaneous amplitude of the arterial pulse produced by that chest compression. The tone frequency varies continuously over a cardiac cycle. Thus, with each chest compression, the higher the tone frequency attained, the larger the arterial pulse produced. In this way a rescuer can vary his/her style of chest compression to obtain the highest pitch tone for each chest compression and thereby maximize the effectiveness of blood pumping. The rescuer hears a variable-frequency whistling sound due to the varying pulse amplitude during chest compression.

Figure 4:
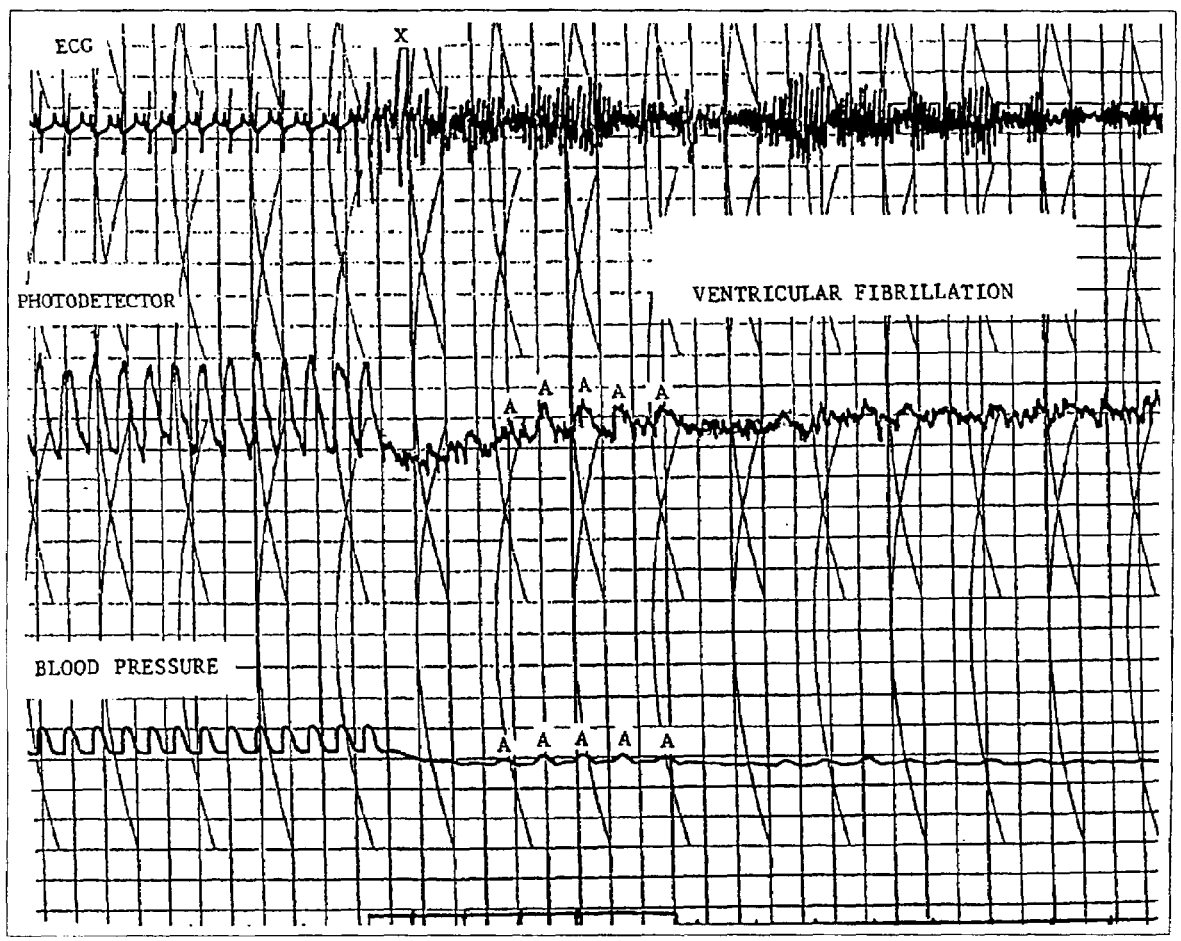
FIGS. 4 and 5 are records of ECG, blood pressure and optical sensor output waveforms obtained prior to and during induced ventricular fibrillation in an animal experiment.
Figure 5:

FIGS. 4 and 5 are records illustrating the use of the optical sensor to detect the arterial pulse produced by rhythmic chest compression during ventricular fibrillation. In these examples, an optical sensor of the type described above was placed on the head of a 16 kg anesthetized pig. FIG. 4 illustrates the ECG, photodetector output pulses and blood pressure with the heart beating normally until point X. The ECG and blood pressure are obtained in a conventional manner. At point X, ventricular fibrillation was induced. Note the immediate changes in the ECG and disappearance of the pulsatile optical pulses and disappearance of pulsatile blood pressure, characteristic of ventricular fibrillation. Observe also, during fibrillation, the small atrial (A) pulses in blood pressure; these are present because the atria are still beating. Note that the optical pickup also detects them. Soon however, the atrial pulses disappear because the atria cease beating with increasing hypoxia.

The record of FIG. 5, made several minutes after that of FIG. 4, shows fibrillation in the ECG, no optical pulses and no pulsatile blood pressure. At the first point C in the graph, chest compressions were commenced which were clearly detected by the optical sensor and are shown in the blood-pressure record. Cessation of chest compression (after 5 compressions) resulted in disappearance of the optical pulses and blood-pressure pulses.

Figure 6:
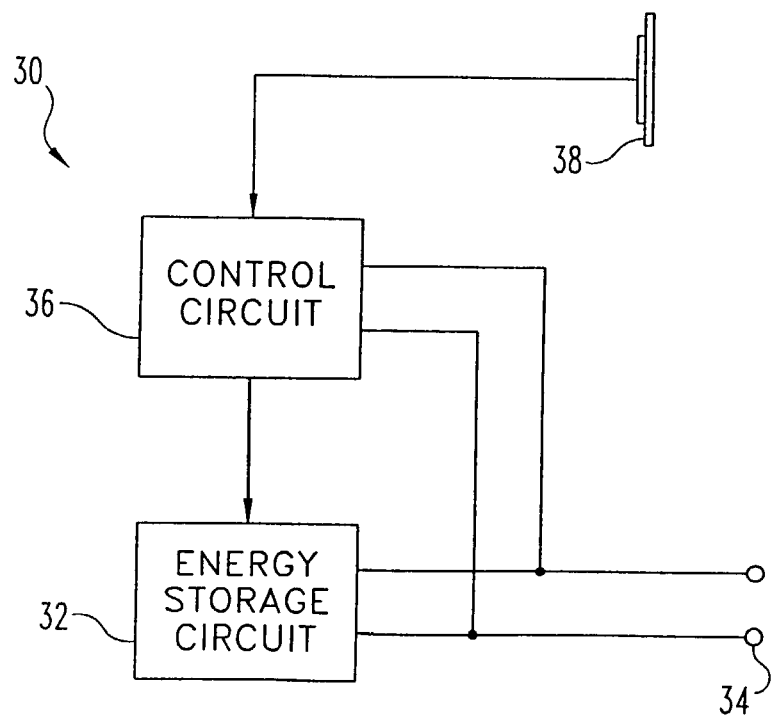
FIG. 6 is a block diagram of an AED equipped with the optical pulse sensor to detect electromechanical dissociation according to the present invention.

Turning now to FIG. 6, an AED 30 according to another embodiment of the present invention includes an energy storage circuit 32, two defibrillation electrodes 34, a control circuit 36 and an optical blood pulse detector 38. The energy storage circuit includes a conventional capacitor network as well as electronically controllable switches for capacitor charging and discharging. The control circuit includes a microprocessor suitably programmed to control the delivery of defibrillation pulses and to analyze the ECG signal obtained from the electrodes. The AED analyzes the frequency of the electrogram and prompts the rescuer to deliver a defibrillation shock if it detects fibrillation in the ECG. Alternatively, the AED may be configured to automatically deliver a shock upon detection of fibrillation.

The optical blood pulse detector, which may be a sensor such as optical sensor 10 placed on the victim's forehead as described above, supplies pulses corresponding to detected arterial pulses to the control circuit, and the control circuit analyzes the input pulses after delivery of a defibrillation shock. The control circuit may be programmed to analyze the pulses from the optical sensor after first analyzing the ECG and determining that the frequency of the electrogram is within a predetermined range indicative of successful defibrillation. The optical blood pulse detector may be connected to the AED control circuit by a cable or, with appropriate modulation/demodulation circuitry, may be connected by a wireless link, e.g., an RF, infrared or ultrasonic link. The AED preferably has a voice chip, i.e., a voice synthesizer integrated circuit, which may be used to generate a tone with varying pitch proportional to arterial pulse amplitude. Alternatively, the AED may be provided with a microphone and audio circuitry for directly responding to the frequency-modulated audible tone from a stand-alone auditory pulse monitor such as described above. If the defibrillation shock achieves the desired result of eliminating the fibrillation but the detected arterial pulse amplitude indicates weak cardiac pumping or no pumping, the control circuit signals the need for CPR. The control circuit may prompt the rescuer with a voice command such as the following: "Defibrillation achieved, resume CPR." The control circuit may be further programmed to detect the absence of QRS waves in the post-defibrillation ECG, indicative of A-V block, or the presence of QRS waves in the post-defibrillation ECG, indicative of electromechanical dissociation (EMD) if there is little or no cardiac pumping, and may issue a corresponding voice command, e.g., "Defibrillation achieved, A-V block present, apply CPR" or "Defibrillation achieved, EMD present, apply CPR." As an alternative to an audible signal, the AED may visually signal the need for CPR, e.g., with an indicator light, preferably a flashing light. Thus, the AED is capable of detecting and appropriately responding to post-defibrillation A-V block and EMD, and could save many lives as a result.

Figure 7:
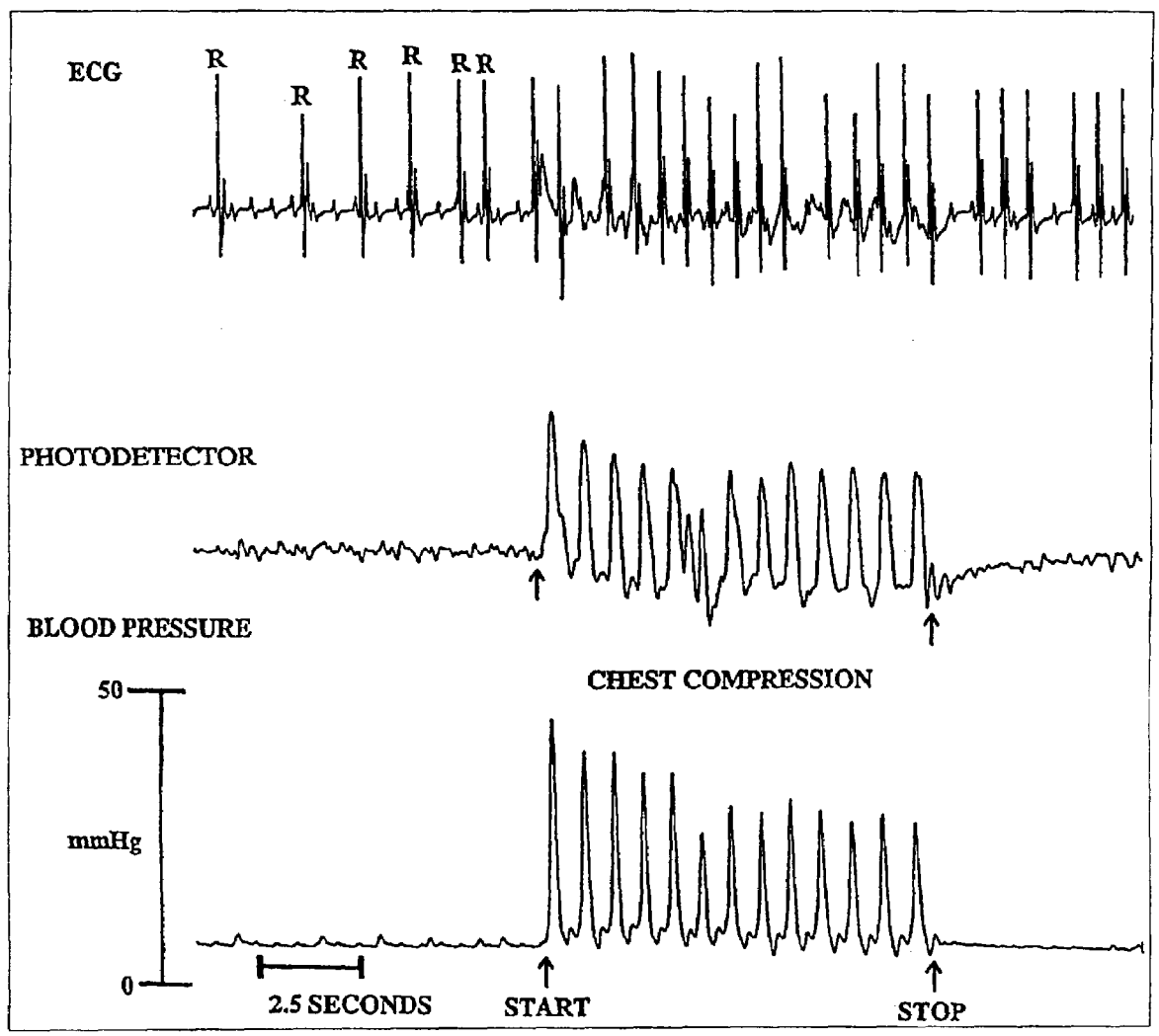
FIG. 7 is a record of waveforms obtained following defibrillation after a period of untreated fibrillation, and shows the presence of EMD and the effect of rhythmic chest compressions revealed in the blood pressure and optical pulse sensor records.

The victim's vulnerability during EMD is illustrated in FIG. 7, which is a record of waveforms obtained following defibrillation after four minutes of untreated (no CPR) ventricular fibrillation. R waves are present in the ECG but the blood-pressure pulses are very weak (or absent), indicating EMD. At the point labeled "Start" in the drawing, rhythmic chest compressions were applied which produced large-amplitude pulses in the blood-pressure record and corresponding optical blood pulses from the photodetector in the optical sensor. The defibrillation shock caused the ECG to return to near normal, and CPR produces a more normal ECG. Very weak pumping after cessation of chest compression at the point labeled "Stop" indicates the need for further CPR.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected. For example, while discussed in relation to a forehead application, an optical sensor such as disclosed above also performs well over the manubrium (top of the sternum), along the sternum to the xiphoid (bottom end of the sternum), and on other body sites where there is a flat bone underlying a tissue bed.

We claim:

1. An auditory pulse monitor for noninvasively detecting the amplitude of arterial pulses in a living subject on a beat-by-beat basis, comprising:
    a light-weight optical sensor including a light source and photodetector adapted for application to a skin surface of said subject over a tissue bed containing an arterial supply, said photodetector generating an output signal proportional to the amplitude of an arterial pulse;
    an electronic circuit connected to said photodetector for generating a signal having a frequency proportional to the instantaneous output signal level of said photodetector, said frequency varying continuously during an individual heartbeat; and
    an audio indicator connected to said electronic circuit for generating an audible tone indicating the amplitude of the arterial pulse.

2. The auditory pulse monitor of claim 1, wherein said optical sensor is adapted to be applied to a skin surface over a tissue bed having a substantially planar underlying bone surface which reflects incident radiation from said light source.

3. The auditory pulse monitor of claim 2, wherein said optical sensor is adapted to be applied to the subject's forehead.

4. The auditory pulse monitor of claim 3, wherein said light source comprises an infrared LED.

5. The auditory pulse monitor of claim 4, wherein said LED has a peak emission wavelength of approximately 800-900 nm.

6. The auditory pulse monitor of claim 4, wherein said LED is pulsed on at a current level greater than approximately 100 mA.

7. The auditory pulse monitor of claim 6, wherein the light from said LED is synchronously detected.

8. The auditory pulse monitor of claim 2, wherein said optical sensor is adapted to be applied to the subject's chest.

9. The auditory pulse monitor of claim 1, wherein said light source comprises an infrared LED with a peak emission wavelength of approximately 800-900 nm.

10. The auditory pulse monitor of claim 1, wherein said circuit is adapted to produce a low-frequency tone in the absence of an arterial pulse when said optical sensor is on the skin surface, and a higher-frequency tone comprising a whistling sound for each arterial pulse.

11. The auditory pulse monitor of claim 1, wherein said light source comprises at least three infrared LEDs equally spaced about said photodetector, said LEDs having a common emission wavelength.

12. An apparatus for noninvasively detecting the amplitude of arterial pulses in a living subject on a beat-by-beat basis, comprising:
    a reflectance-type optical sensor including a light source and photodetector adapted for application to a skin surface of said subject over a tissue bed containing an arterial supply; and
    indicator means responsive to a signal from said photodetector for generating a variable-frequency audible indication of the beat-by-beat amplitude of said arterial pulses with said optical sensor held stationary on the skin with substantially constant pressure, said audible indication varying continuously during a single heartbeat in proportion to the instantaneous output signal from said photodetector.

13. The apparatus of claim 12, wherein said optical sensor is adapted to be applied to a skin surface over a tissue bed having a substantially planar underlying bone surface which reflects incident radiation from said light source, and wherein said optical sensor is adapted for operative placement over said tissue bed and bone surface during a condition of pulseless electrical activity.

14. The apparatus of claim 13, wherein said optical sensor is adapted to be applied to the subject's forehead.

15. The apparatus of claim 14, wherein said light source comprises an infrared LED.

16. The apparatus of claim 15, wherein said LED has a peak emission wavelength of approximately 800-900 nm.

17. The apparatus of claim 15, wherein said LED is pulsed on at a current level greater than approximately 100 mA.

18. The apparatus of claim 17, wherein the light from said LED is synchronously detected.

19. The apparatus of claim 13, wherein said optical sensor is adapted to be applied to the subject's chest.

20. The apparatus of claim 12, wherein said indicator means produces a low-frequency tone in the absence of an arterial pulse when said optical sensor is on the skin surface, and a higher-frequency tone comprising a whistling sound for each arterial pulse.

21. The apparatus of claim 12, wherein said light source comprises at least three infrared LEDs equally spaced about said photodetector, said LEDs having a common emission wavelength.

22. An auditory method of noninvasively detecting the amplitude of arterial pulses in a living subject on a beat-by-beat basis, comprising:
    applying an optical sensor including a light source and photodetector to a skin surface of said subject over a tissue bed containing an arterial supply so as to generate an output signal from said photodetector which is proportional to the amplitude of an arterial pulse;
    generating an electrical signal having a frequency proportional to the instantaneous output signal level of said photodetector, said frequency varying continuously during an individual heartbeat; and
    generating an audible tone in response to said electrical signal to indicate the amplitude of the arterial pulse.

23. The auditory method of claim 22, wherein said optical sensor is applied to a skin surface over a tissue bed having a substantially planar underlying bone surface which reflects incident radiation from said light source, and wherein said generating step includes generating said electrical signal with continuously varying frequency while said optical sensor is stationary on the skin.

24. The auditory method of claim 23, wherein said optical sensor is applied to the subject's forehead.

25. The auditory method of claim 24, wherein said light source comprises an infrared LED.

26. The auditory method of claim 25, wherein said LED has a peak emission wavelength of approximately 800-900 nm.

27. The auditory method of claim 25, wherein said LED is pulsed on at a current level greater than approximately 100 mA.

28. The auditory method of claim 27, wherein the light from said LED is synchronously detected.

29. The auditory method of claim 23, wherein said optical sensor is applied to the subject's chest.

30. The auditory method of claim 22, wherein said generating step includes generating a low-frequency tone in the absence of an arterial pulse when said optical sensor is on the skin surface, and a higher-frequency tone comprising a whistling sound for each arterial pulse.

31. The method of claim 22, wherein said light source comprises at least three infrared LEDs equally spaced about said photodetector, said LEDs having a common emission wavelength.

32. A method for noninvasively detecting the amplitude of arterial pulses in a living subject on a beat-by-beat basis, comprising:
    applying a reflectance-type optical sensor including a light source and photodetector to a skin surface of said subject over a tissue bed containing an arterial supply; and
    generating a variable-frequency audible indication of the beat-by-beat amplitude of said arterial pulses based on a signal from said photodetector while it is held stationary on the skin with substantially constant pressure, said audible indication varying continuously during a single heartbeat in proportion to the instantaneous output signal from said photodetector.

33. The method of claim 32, wherein said optical sensor is applied to a skin surface over a tissue bed having a substantially planar underlying bone surface which reflects incident radiation from said light source.

34. The method of claim 33, wherein said optical sensor is applied to the subject's forehead.

35. The method of claim 34, wherein said light source comprises an infrared LED.

36. The method of claim 35, wherein said LED has a peak emission wavelength of approximately 800-900 nm.

37. The method of claim 35, wherein said LED is pulsed on at a current level greater than approximately 100 mA.

38. The method of claim 37, wherein the light from said LED is synchronously detected.

39. The method of claim 33, wherein said optical sensor is applied to the subject's chest.

40. The method of claim 32, wherein said generating step includes generating a low-frequency tone in the absence of an arterial pulse when said optical sensor is on the skin surface, and a higher-frequency tone comprising a whistling sound for each arterial pulse.

41. The method of claim 32, wherein said light source comprises at least three infrared LEDs equally spaced about said photodetector, said LEDs having a common emission wavelength.

42. A method of providing feedback to a rescuer on effectiveness of chest compressions performed on a subject during external CPR, comprising:
    applying an optical sensor including a light source and matched photodetector to a skin surface of said subject over a tissue bed containing an arterial supply so as to generate an output signal from said photodetector which is proportional to the amplitude of an arterial pulse produced by external chest compression performed on said subject during external CPR; and
    generating a variable-frequency feedback indication in response to said output signal indicative of the amplitude of the arterial pulses produced by said external chest compressions, said feedback indication varying continuously in frequency during a single heartbeat in proportion to the instantaneous output signal from said photodetector.

43. The method of claim 42, wherein the optical sensor is applied to a skin surface over a tissue bed having a substantially planar underlying bone surface which reflects incident radiation from said light source.

44. The method of claim 43, wherein the optical sensor is applied to the subject's forehead.

45. The method of claim 44, wherein said light source is an infrared source.

46. The method of claim 42, wherein the step of generating a feedback indication includes generating an audible signal.

47. The method of claim 46, wherein the step of generating an audible signal includes generating an audible tone.

48. The method of claim 47, wherein the step of generating an audible tone includes generating an audible tone having a frequency that varies with the amplitude of the arterial pulses produced by said chest compressions.

49. The method of claim 42,
wherein said output signal from said photodetector is supplied to a defibrillator having defibrillation electrodes, separate from said optical sensor, for placement on the subject for ECG signal pickup and delivery of defibrillation pulses, and
wherein said feedback indication is generated via said defibrillator based on an analysis of said output signal from said photodetector.

50. A method for indicating the effectiveness of chest compressions performed on a subject during external CPR, comprising:
applying a reflectance-type optical sensor including a light source and photodetector to a skin surface of said subject over a tissue bed containing an arterial supply; and
generating a variable-frequency indication of the amplitude of arterial pulses produced by said chest compressions during external CPR based on a signal from said photodetector, said indication varying continuously in frequency during a single heartbeat in proportion to the instantaneous output signal from said photodetector.

51. The method of claim 50, wherein said optical sensor is applied to a skin surface over a tissue bed having a substantially planar underlying bone surface which reflects incident radiation from said light source.

52. The method of claim 51, wherein said optical sensor is applied to the subject's forehead.

53. The method of claim 52, wherein said light source comprises an infrared LED.

54. The method of claim 50, wherein the step of generating an indication includes generating an audible indication.

55. The method of claim 54, wherein the step of generating an audible indication includes generating an audible tone having a frequency which varies with the amplitude of the arterial pulses.

56. The method of claim 50,
wherein said signal from said photodetector is supplied to a defibrillator having defibrillation electrodes, separate from said optical sensor, for placement on the subject for ECG signal pickup and delivery of defibrillation pulses, and
wherein said indication is generated via said defibrillator based on an analysis of said output signal from said photodetector.

* * * * *